US009623197B2

(12) United States Patent
Jia et al.

(10) Patent No.: US 9,623,197 B2
(45) Date of Patent: Apr. 18, 2017

(54) PRESSURIZED MEDICAL INSTRUMENT

(71) Applicant: Beijing Demax Medical Technology Co., Ltd., Beijing (CN)

(72) Inventors: Deng Qiang Jia, Beijing (CN); Qiang Li, Beijing (CN); Zhen Shan Bao, Beijing (CN)

(73) Assignee: BEIJING DEMAX MEDICAL TECHNOLOGY CO., LTD., Beijing (CN)

( * ) Notice: Subject to any disclaimer, the term of this patent is extended or adjusted under 35 U.S.C. 154(b) by 925 days.

(21) Appl. No.: 13/923,929

(22) Filed: Jun. 21, 2013

(65) Prior Publication Data
US 2014/0074026 A1 Mar. 13, 2014

(30) Foreign Application Priority Data
Sep. 13, 2012 (CN) .......................... 2012 1 0339612

(51) Int. Cl.
*A61M 5/48* (2006.01)
*A61M 5/315* (2006.01)
*A61M 5/31* (2006.01)

(52) U.S. Cl.
CPC ........ *A61M 5/482* (2013.01); *A61M 5/31501* (2013.01); *A61M 5/31511* (2013.01); *A61M 5/484* (2013.01); *A61M 2005/3125* (2013.01); *A61M 2205/3344* (2013.01)

(58) Field of Classification Search
CPC ...... A61M 5/482; A61M 5/484; A61M 5/488; A61M 5/48; A61M 5/486; A61M 5/142; A61M 5/16854
See application file for complete search history.

(56) References Cited

U.S. PATENT DOCUMENTS

| 4,654,027 A * | 3/1987 | Dragan ............. | A61M 25/1018 137/614.2 |
| 5,137,514 A * | 8/1992 | Ryan ................. | A61M 25/1018 604/100.01 |
| 2005/0263109 A1* | 12/2005 | Daniels .................... | F01P 11/18 123/41.15 |
| 2009/0227947 A1* | 9/2009 | Caclin ............... | A61M 25/1018 604/97.02 |
| 2012/0316507 A1* | 12/2012 | Agard ................ | A61B 17/8819 604/187 |

* cited by examiner

*Primary Examiner* — Bhisma Mehta
*Assistant Examiner* — Hamza Darb
(74) *Attorney, Agent, or Firm* — Dorsey & Whitney LLP

(57) ABSTRACT

A pressurized medical instrument may include a piston handle system, a locking release system and a pressure display system. The piston handle system may include a piston, a piston seal, a handle and a rear cover. The locking release system may include a push button, a fixed support, a locking block, one or more springs and a slide block. The pressure display system may include a coating, a gauge stand, a lateral board, a gauge stand seal ring, a pressure gauge seal ring, a snapper, a pressure gauge and a rotary Luer conical tapered fitting. The pressurized medical instrument may facilitate rapid boosting operation by two hands, vacuum pumping by two hands and rapid pressure relief by a single hand. The instrument is characterized by ease-of-operation, quick boosting and pressure relief for observing easily the pressure value at different operating angles.

13 Claims, 4 Drawing Sheets

PRESSURIZED MEDICAL INSTRUMENT

FIELD OF THE INVENTION

The present invention relates to the technology of a medical instrument, and more particularly to one which is used for pressure charging and relief.

BACKGROUND

In a number of medical and surgical procedures, human body parts or lumens are expanded, using expansion devices. For example, expansion of inherent human lumens or channels such as narrow blood vessels, nasolacrimal ducts and fallopian tubes, or even expansion of bone-loosening parts or other tissues and human structures, is often an important means of medical treatment. Generally, these an instrument capable of pressure charging and relief is required for such procedures. For instance, when conducting coronary artery intervention operations, a pressurized instrument is required for pressurized expansion of a balloon catheter and/or intravascular stents. After that, other one-time auxiliary instruments are removed through relief and vacuum pumping. While conducting peripheral vascular intervention therapies and vertebral intervention therapies, an instrument capable of pressure charging and relief is required, with some kind of displayed pressure value, enabling the medical staff to observe the charging pressure. Often guided by medical imaging (X-ray, ultrasound, CT, etc.), such surgery is conducted in such a manner that a special catheter or device is inserted into the lesions for imaging and diagnostics through a percutaneous puncturing approach or natural human orifices, allowing for pressurized expansion and relief.

Currently, cardiac intervention therapy, neurological intervention therapy, cerebrovascular intervention therapy, peripheral vascular therapy, and non-vascular lumen intervention therapies are widely used by inserting the catheter and guide wire into the lesions through natural human lumens. Under the guidance and monitoring of medical imaging devices, a pressurized instrument is used for expansion and negative vacuum pumping of other instruments to restore the human lumens.

Existing pressurized instruments have a number of shortcomings. For example, many of them are difficult operate, are slow/difficult to pressurize, are not able to reach high pressure, have too much sliding resistance of the piston, cause bubble formation, and/or it is not possible to relieve pressure in the device with a single hand. With a growing range of interventional therapies, there is an increasing demand for pressurizing instruments. Especially for vascular interventional treatments, air bubble generation, expansion times and boosting speeds should ideally be strictly controlled.

The purpose of the present invention is to design a pressurized medical instrument for meeting the detailed requirements in clinical applications; it's characterized by multi-angle observation of the pressure display, single-hand quick relief, smaller pressurization resistance, ease-of-operation, good stability and security.

SUMMARY OF THE INVENTION

The present invention enables users to observe the pressure display at multiple angles, which accommodates the typical methods of use of the medical staff, who may, where applicable, rotate transversely the pressure display to realize the optimum viewing angle.

The present invention features two-hand quick boosting speed, smaller pressurization resistance, and stable and reliable pressure locking. In clinical operations, the user may hold the coating by one hand, and hold the handle to rotate it clockwise by the other hand and quickly pressurize to the full stroke with stable and reliable locking functions. Meanwhile, the pressure locking function may be removed to realize instant pressure relief by pressing the push button with the thumb or palm of the hand holding the coating. Alternatively, the user may press the push button and pull freely the handle by the other hand to pump mechanically the liquid or release liquid.

To this end, the pressurized medical instrument of the present invention includes a handle piston system, a locking release system and a pressure display system.

In one embodiment, the handle piston system includes a piston and a groove on its external surface mated with the piston seal. Its rear end is mated with the front section of the handle. The piston and piston seal are coaxially mated at inner wall of the coating. While sealing fitness with the inner wall of the coating is ensured under high pressure and negative pressure, the piston and piston seal can slide on the inner wall of the coating, meeting the maximum capacity of the piston sliding up to 60 ml.

In one embodiment, the handle has a male thread that's mated with the female thread of the locking block. The starting position of the front thread is disengaged from the female thread of the locking block when the piston moves to the maximum capacity of the coating. The stopping position of the rear thread could at least meet the requirement that the thread of the handle is fully meshed with that of the locking block when the piston moves to the zero scale of the coating. A conical disk with maximum diameter of about 48 mm is located at a rear section of the handle, with its shape fully coupled with the hand pattern. This helps to rotationally pressurize the handle by hands, and when a smaller force is applied, the torque converted to the thread of the handle is big enough to overcome the resistance generated from pressurization.

In one embodiment, the pressure display system may include a coating. An inner chamber of diameter of about 15-35 mm is set at its front end, with the length sufficient to form a maximum capacity of about 60 ml. A cavity is set at its rear end and can be mated with the fixed support and rear cover with respect to the shape and structure. The rear end of the coating has a shape designed to work ergonomically with the human hand, allowing a user to operate and hold the device easily and comfortably with safety and reliability. The external surface of the front end of the coating is mated with the inner surface of the gauge stand, and the gauge stand can rotate transversely along the axle of the coating while guaranteeing sealing fitness.

In one embodiment, bulges mated with the coating are set on the fixed support. When the product is pressurized by turning the handle, the bulges of the fixed support are tightly mated with the notches of the coating, avoiding disengagement of the fixed block from the coating. Two axle holes are set on upper end of the fixed support, and used for fixing the handle when the handle passes through it. Notches mated with the bulges of the locking block are set at both sides of the fixed support; when the spring is loaded from the bottom of the locking block, then compressed and installed into the fixed support, the bulges at both sides of the locking block are mated with the notches at both sides of the fixed support, preventing the spring from bouncing out of the locking block. A through-hole of the same shape with the slide block is separately set at both sides of the locking block above the bulges. When two slide blocks are installed from both sides, and the spring is installed from the middle, the inclined surface of moveable block faces upwards. When the handle passes through the coaxial hole on upper end of the fixed support, the handle will compress the locking block and drive two slide blocks downwards to compress the inner spring. Finally, the bottom of two slide blocks gets into touch with the steps at both sides of the fixed support, restricting the locking block from moving downwards. In such a case, the female thread of the locking block is fully meshed with the male thread of the handle.

In one embodiment, the push button is mounted onto the coating through the holes on the coating. Two bulges are set at both sides and mated with the coating holes by snapper, preventing disengagement of the push button from the coating. There are two presser feet at both sides below the push button, with an inclined inner surface. After completion of assembly, the inclined surface of the presser feet gets into touch with the inclined surface of side slide blocks; when pressing the push button, the inclined surface of the presser feet compresses the inclined surface of the slide blocks, driving two slide blocks to move inwards and compress the spring continuously. If the user continues to press the push button, the square plane of the push button compresses the plane of the locking block. In such a case, the sides of two slide blocks are compressed by the push button until its bottom is disengaged from the steps of the fixed support, and the locking block drives the slide blocks to move downward until the female thread of the locking block is fully separated from the male thread of the handle, realizing the release functions of the locking release system. In such a case, rapid pressure relief of the instrument may be accomplished, and at the same time, the handle may slide freely within the effective stroke in the cavity of the coating, along with the piston and piston seal. If the push button is released, all mechanisms are restored to their initial state under the action of two springs, realizing the locking function of the locking release system.

In one embodiment, a bulge is set on the handle. After completion of assembly, the handle is rotated clockwise, and the bulge's male thread may be limited into the groove on the rear cover. In such a case, the piston is located on the zero scale of the coating, so the handle could only be rotated counterclockwise, thus avoiding effectively the contact extrusion of the front end of the piston with the end surface of the coating.

These and other features and embodiments are described in further detail below, in reference to the attached drawing figures.

DETAILED DESCRIPTION OF THE INVENTION

Figure 1:
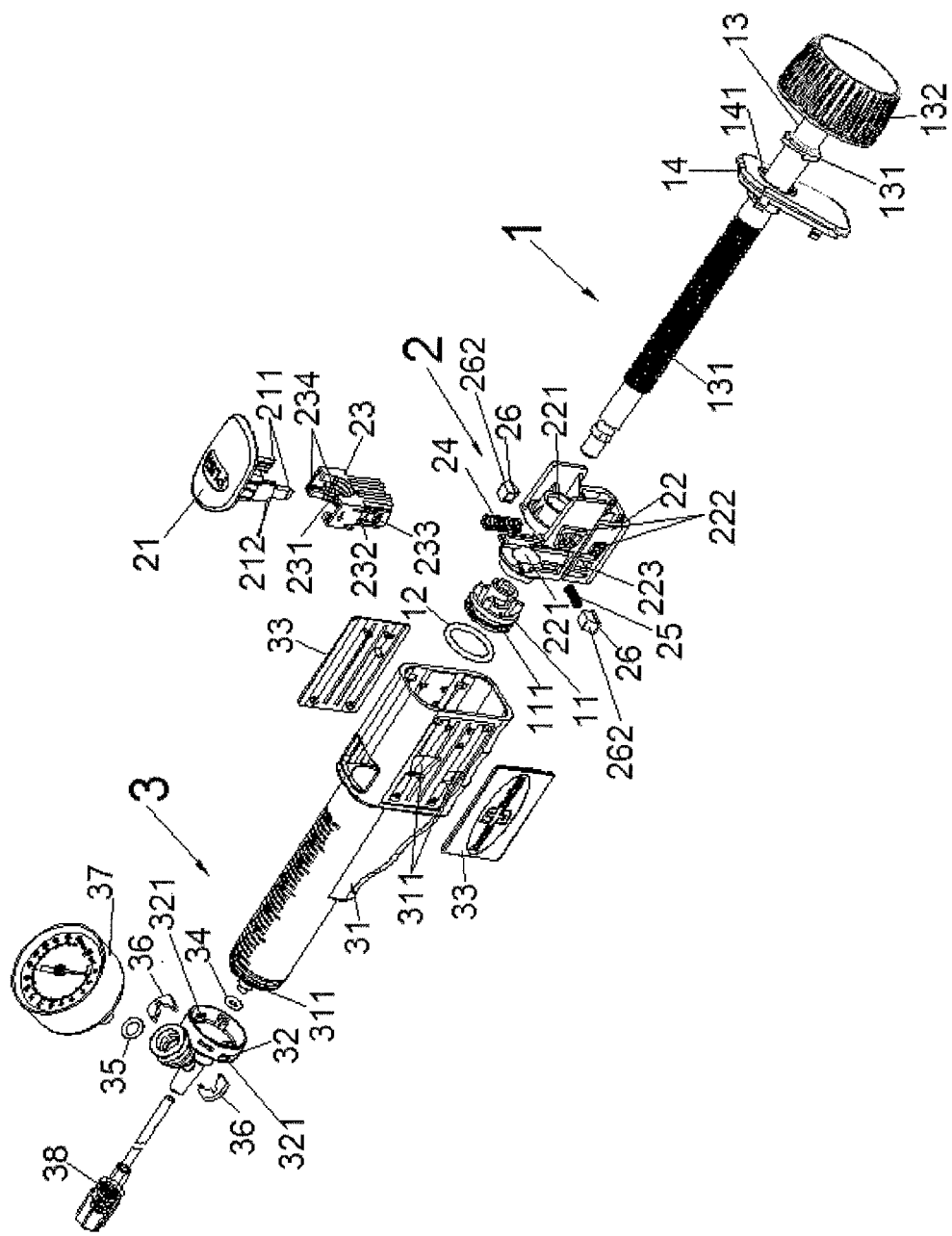
FIG. 1 is an exploded view of a pressurized medical instrument, according to one embodiment.
Figure 2:
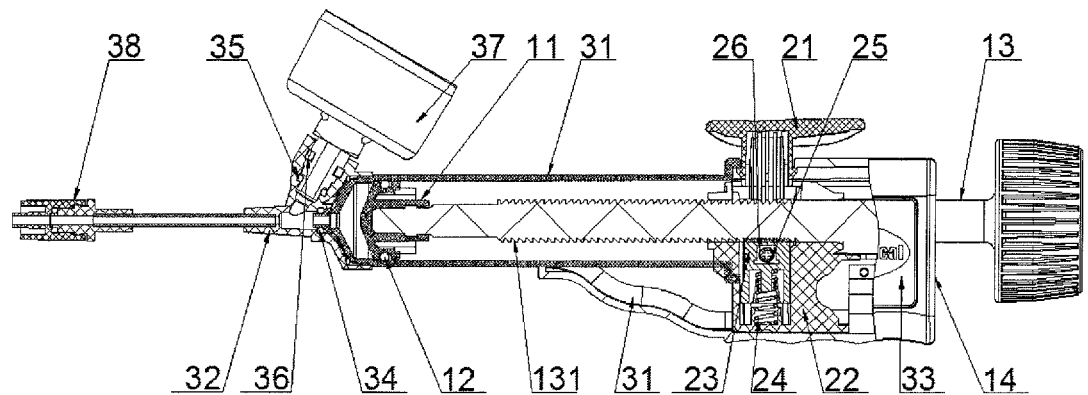
FIG. 2 is a side, partial cross-sectional view of the pressurized medical instrument of FIG. 1.

The features and advantages of the various embodiments will be more readily understood upon a thoughtful deliberation of the following detailed description of one embodiment of a pressurized medical instrument, with reference to the accompanying drawings.

In one embodiment of the pressurized medical instrument, its maximum capacity is about 60 ml, and its maximum charging pressure is about 30 atm. In this or alternative embodiments, the pressurized medical instrument may have a locking release system that can lock the piston of the instrument at a capacity of about 0-60 ml and a charging pressure of about 0-30 atm.

Referring to FIGS. 1-8, one embodiment of a pressurized medical instrument may include a piston handle system 1, a locking release system 2 and a pressure display system 3. The piston handle system 1 may include a piston 11, a piston seal 12, a handle 13 and a rear cover 14. The locking release system 2 may include a push button 21, a fixed support 22, a locking block 23, a spring 24, a spring 25 and a slide block 26. The pressure display system 3 may include a coating 31, a gauge stand 32, a lateral board 33, a gauge stand seal ring 34, a pressure gauge seal ring 35, a snapper 36, a pressure gauge 37 and a rotary Luer conical tapered fitting 38.

Figure 7:
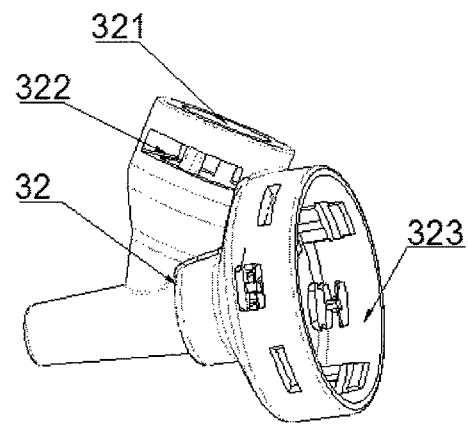

Referring to FIG. 7, in one embodiment, the gauge stand 32 is fitted with mounting hole 321 for the pressure gauge 37, the mounting hole 322 for the snapper 36 and the hole 323 mated with the coating 31. The pressure gauge 37 and pressure gauge seal ring 35 are installed into the mounting hole 321 of the gauge stand 32, the mounting holes 322 of two snappers 36 and the gauge stand 32 are mated to restrict the disengagement of the pressure gauge 37 from the gauge stand 32. The gauge stand 32 and the gauge stand seal ring 34 are installed at front end of the coating 31, and also mated tightly with the coating 31. The gauge stand 32 drives the pressure gauge 37 to rotate coaxially along the coating 31, enabling a user to select a desired angle at which to observe the display value of the pressure gauge 37.

Figure 8:
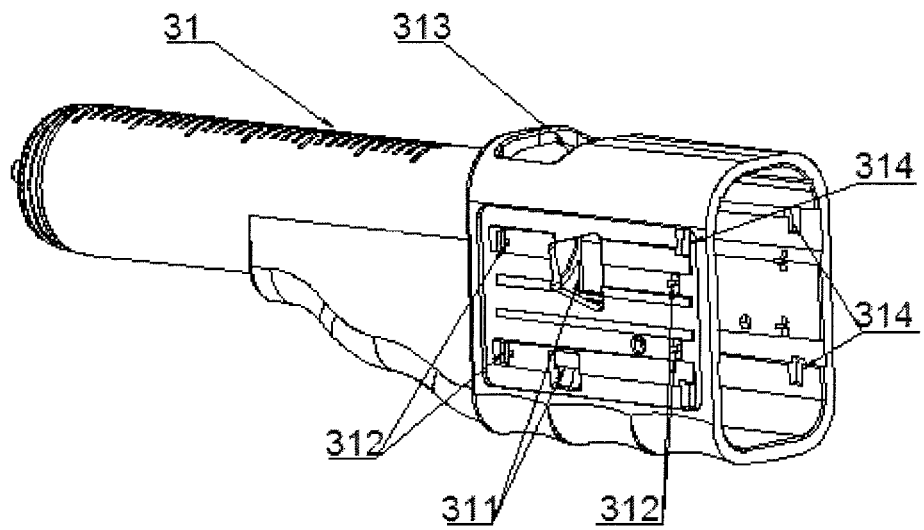

Referring to FIG. 8, in one embodiment, when holding the coating 31, the shape of the coating 31 is designed to adapt to the hand pattern for a better sense of touch. Two mounting holes 311 for the fixed support 22 and two mounting holes 312 for the lateral board 33 are set at both sides of the coating 31, while the mounting hole 313 for the push button 21 and the mounting hole 314 for the rear cover 14 are set above the coating 31. The coating is provided with scale showing the capacity of inner cavity, (unit: ml). The inner cavity of the coating 31 forms an interference fit with the piston seal 12.

Figure 3:
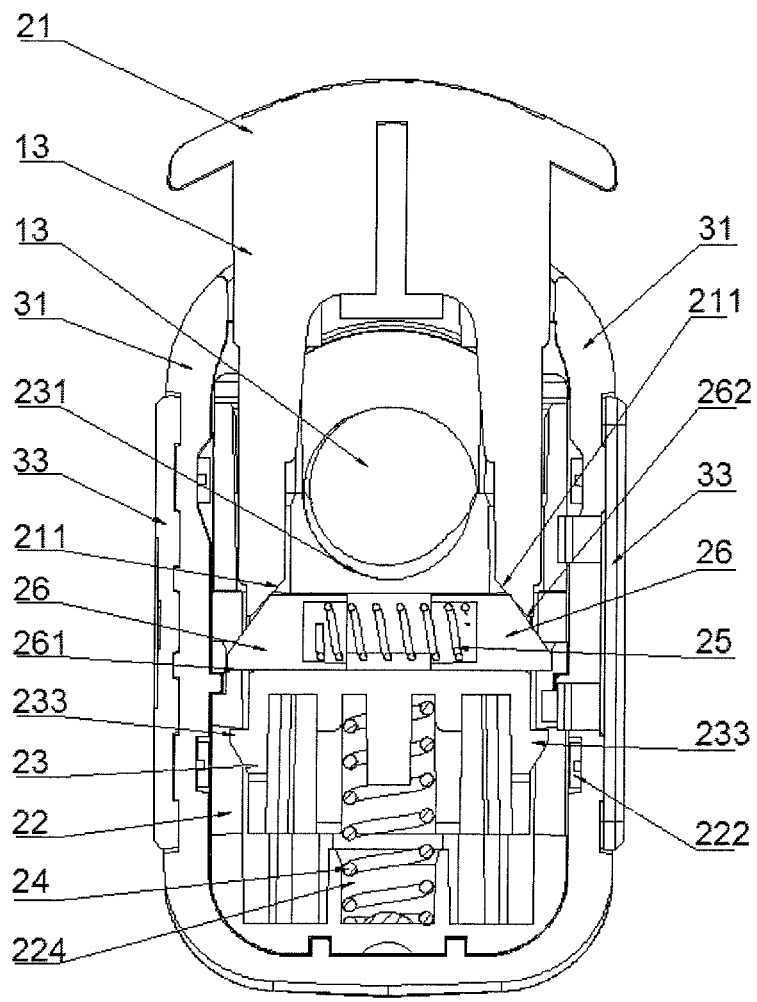
FIG. 3 is an end-on, cross-sectional view of a locking release system of the pressurized medical instrument of FIGS. 1 and 2.
Figure 4:
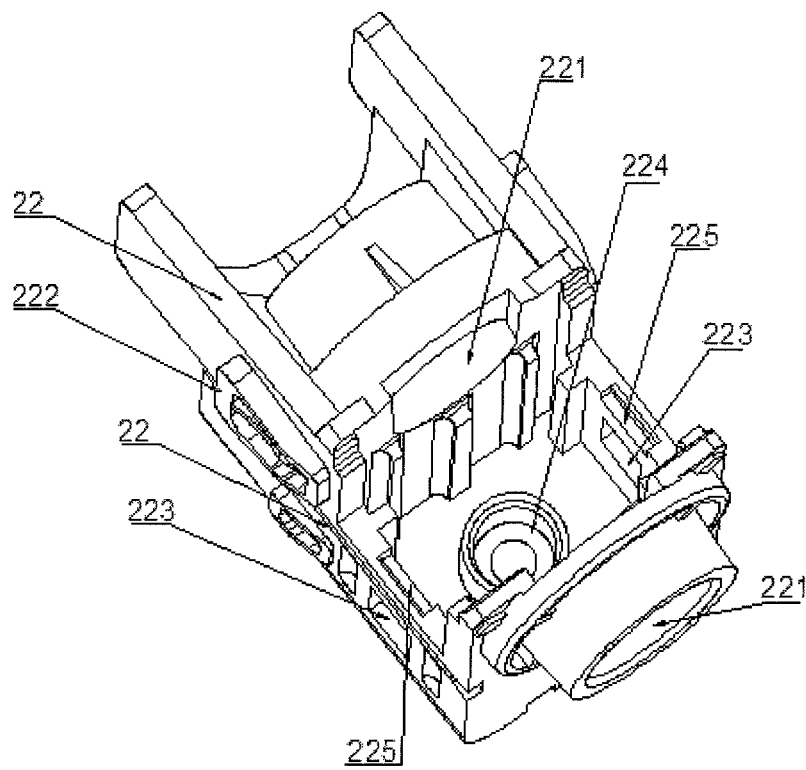
FIGS. 4-8 are perspective views of various component parts of the pressurized medical instrument of FIGS. 1-3.

Referring to FIGS. 3 and 4, in one embodiment, the fixed support 22 may act as a support member, to which the handle 13, push button 21, slide block 26, spring 24, locking block 23 and coating 31 are mated together. A bulge 222 for mating with the mounting hole 311 of the coating 31 and mounting holes 223 for mating with the block 23 are set at both sides. Steps 225 for limiting the slide block 26 are set at both upper sides. Two mounting holes 221 for the handle 13 are set at front and rear sides, and a pit 224 for the spring 24 is set at inner bottom.

Figure 5:
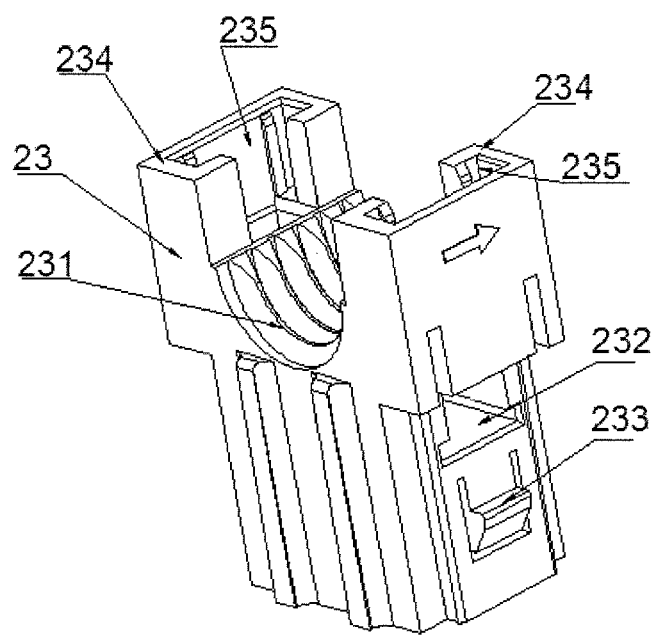
Figure 6:
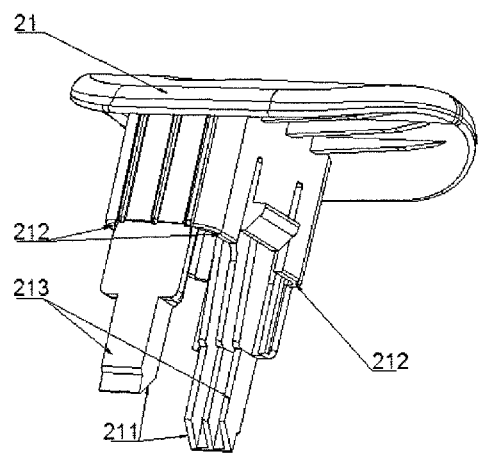

Referring to FIG. 5, in one embodiment, bulges 233 mating with the mounting hole 223 of the fixed support 22 are set at both sides of the locking block 23. Through-holes 232 of the same shape with the slide block 26 are set above the bulges 223. Semicircular female thread 231 mating with the male thread 131 of the handle 13 is set on the locking block 23. The upper surface 234 of the locking block 23 is provided with two longitudinal grooves 235. After completion of assembly, two presser feet 213 of the push button 21 separately pass through two longitudinal grooves 235 of the locking block 23 and make two planes 212 of the push button 21 run parallel with the upper surface 234 of the locking block 23. When the push button 21 is pressed, two planes 212 of the push button 21 come into contact with the upper surface 234 of the locking block 23, driving the locking block 23 downwards.

Referring to FIG. 3, in one embodiment, the slide block 26 has an inclined surface 262 and a bottom surface 261. Two slide blocks 26 are installed separately from both sides of the through-hole 232 of the locking block 23, and a spring 25 is installed at middle of two slide blocks 26, such that the inclined surface 262 of two slide blocks 26 faces outwards and upwards. One end of the spring 24 is installed into the pit 224 of the fixed support 22, and the other end installed into the bottom of the locking block 23, then the slide block 26 is extruded from both sides to compress the spring 25, the locking block 23 and spring 24. So, two bulges 233 of the locking block 23 are assembled into two mounting holes 223 at both sides of the fixed support 22, while the locking block 23 is fixed into the fixed support 22, the bottom and sides of two slide blocks 26 just come into contact with two steps 225 at both sides of the fixed support 22. In such case, the locking block 23 is completely fixed into the fixed support 22 without any displacement.

In one embodiment, the rear cover 14 is threaded onto the handle 13, and four snappers face the front end of the handle 13.

In one embodiment, two presser feet 213 of the push button 21 are installed into two longitudinal grooves 235 of the locking block 23, and the locking block 23 shifts downwards if the push button 21 is pressed. In such a case, the front end of the handle 13 with a rear cover 14 is inserted into the rear mounting hole 221 of the fixed support 22 and then into the front mounting hole 221 of the fixed support 22. When the push button 21 is released, the locking block 23 moves upwards, with its female thread 231 fully meshed with the male thread 131 of the handle 13.

In one embodiment, the front end of the handle 13 is installed on the piston 11, and a piston seal 12 is installed into the groove 111 of the piston 11. The assembled locking release system 2 and piston handle system 1 are installed into the cavity of the coating 31, such that four bulges 222 of the fixed support 22 are locked into four mounting holes 311 of the coating 31. Two lateral boards 33 are installed at both sides of the coating 31, such that the mounting bulge of the lateral boards 33 is locked into the mounting hole 312 of the coating 31. The rear cover 14 is locked into the mounting hole 314 of the coating 31. The push button 21 is installed into the mounting hole 313 above the coating 31, and the bulge of the push button 21 is locked into the mounting hole 313 of the coating 31. Thus, the pressurized medical instrument of the present invention is shaped.

One advantage of one embodiment of the pressurized medical instrument is that the locking release system can lock the handle in a pressurized state by two springs mated with special structures. For instance, the slide block's inclined surface, the fixed support's steps and mounting hole, the locking block's thread, and/or the groove and snapper may convey the instrument with stable and reliable pressure locking functions.

Another advantage of one embodiment of the pressurized medical instrument is that when the push button is pressed with the thumb or palm of the hand holding the coating, the push button drives the slide block and locking block in different directions, so the locking of the locking block and handle can be removed to quickly release the pressure of instrument with a single hand.

One advantage of one embodiment of the pressurized medical instrument is that the pressure gauge along with the gauge stand can rotate along the axle of the coating, enabling the medical staff to select a desired or optimum viewing angle and avoid reading error.

In one embodiment, the pressurized medical enables pressure charging by rotating the handle clockwise and pressure relief or vacuum pumping by rotating the handle counterclockwise. By pressing the push button, the handle can be turned to maximum capacity. By releasing the push button, quick liquid pumping or vacuum pumping can be conducted. If pressing push button to push the handle to the zero capacity, the medium in the cavity of the coating can be quickly discharged, or the vacuum can be rapidly pumped out. In alternative embodiments, the rotating directions of the locking block and handle thread may be changed, so as to change the rotating direction of the handle during pressure charging and relief.

In one embodiment, the pressurized medical instrument may have a maximum capacity of about 60 ml and a maximum charging pressure of about 30 atm. In alternative embodiments, the structure and design of the pressurized medical instrument are not limited by the aforementioned ranges, and the size and number of relevant component parts may be increased as necessary.

While the invention has been particularly shown and described with reference to embodiments thereof, various changes in form and details may be made therein without departing from the spirit and scope of the invention.

The invention claimed is:

1. A pressurized medical instrument, comprising:
 a piston handle system at a first end of the pressurized medical instrument, wherein the piston handle system comprises a handle;
 a locking release system mated with the piston handle system such that turning the handle of the piston handle system pressure charges the medical instrument, the locking release system comprising:
  a push button;
  a fixed support;
  a locking block having a semicircular female thread on an upper end;
  a first spring;
  a second spring; and
  a slide block; and
 a pressure display system at a second end of the pressurized medical instrument, opposite the first end, the pressure display system comprising:
  a coating having a shape configured to adapt to a hand pattern for a better sense of touch;
  a gauge stand attached to the coating; and
  a pressure gauge attached to the gauge stand, wherein the gauge stand is configured to drive the pressure gauge to rotate co-axially along the coating, enabling a user to select a desired angle at which to observe a display value of the pressure gauge,
 wherein the handle, the push button, the slide block, the first spring, the locking block, and the coating are mated together via the fixed support of the locking release system,
 wherein the locking block of the locking release system comprises a through-hole,
 wherein the locking release system includes two slide blocks, each of which comprises an inclined surface, and each of which is separately fitted into one of two opposite ends of the through-hole of the locking block, and wherein the second spring is located between and compressed by the two slide blocks.

2. The instrument as in claim 1, wherein the piston handle system further comprises:
   a piston coupled with the handle during pressure charging and relief, such that the piston rotates freely on the handle;
   a piston seal embedded into a groove on a peripheral surface of the piston and mated with an inner wall of the coating; and
   a rear cover,
   wherein a male thread on a surface of the handle mates with the female thread of the locking block.

3. The instrument as in claim 2,
   wherein the handle of the piston handle system comprises a conical disk located on a rear section of the handle such that the handle can be rotated by holding the conical disk, and
   wherein the male thread of the handle of the piston handle system is configured to avoid deformation or rupture of a tip of the male thread when charging the instrument to above about 30 atm of pressure.

4. The instrument as in claim 3, wherein the male thread of the handle of the piston handle system is located on the handle such that when the handle is rotated clockwise until the male thread comes into contact with a grooved thread on the rear cover of the piston handle system, the clockwise rotation of the handle is stopped, the piston is at a zero scale, and the handle is only able to rotate counterclockwise.

5. The instrument as in claim 3,
   wherein clockwise rotation of the handle causes pressurization of the instrument and counterclockwise rotation of the handle causes pressure relief from the instrument, and
   wherein, when the piston and the handle move to a maximum stroke, the male thread of the handle is disengaged from the female thread of the locking block, thus preventing shedding when the piston rotates the handle counterclockwise to the maximum stroke.

6. The instrument as in claim 1, wherein the pressure display system further comprises:
   a lateral board;
   a gauge stand seal ring;
   a pressure gauge seal ring;
   a snapper; and
   a rotary Luer conical tapered fitting,
   wherein the gauge stand is mated with the coating and the gauge stand seal ring.

7. The instrument as in claim 6, wherein a maximum capacity of the pressurized instrument is about 60 ml, wherein a maximum charging pressure of the pressurized instrument is about 30 atm, and wherein, when the pressurized instrument is filled with a liquid medium, the rotary Luer conical tapered fitting for blocking the instrument allows the handle to rotate clockwise two turns, and a pressure value displayed on the pressure gauge is at least about 15 atm.

8. The instrument as in claim 1, wherein the pressure gauge includes a fluorescent display.

9. The instrument as in claim 1, wherein the pressure display system further comprises grooves on a periphery of the coating, wherein the gauge stand includes two bulges mated with the grooves, and wherein, when the gauge stand is rotated, the bulges slide from one groove to another groove, such that the gauge stand is configured to be rotated and to be fixed into any of the grooves.

10. The instrument as in claim 1,
    wherein the fixed support includes a pit for fixing a first end of the first spring,
    wherein a second end of the first spring is installed into a bottom of the locking block, and
    wherein the two slide blocks compress the first spring, the locking block and the second spring.

11. The instrument as in claim 10, wherein two holes pass through the handle, wherein a front end of the handle passes through two holes of the fixed support in succession and compresses the locking block, and wherein the female thread of the locking block meshes with a male thread of the handle.

12. The instrument as in claim 1, wherein an exterior of the fixed support includes a bulge configured to mate via interference fit with mating holes at opposite sides of the coating.

13. The instrument as in claim 1, wherein the push button is configured to drive the slide block and locking block in different directions, to allow the locking block and the handle to be removed to quickly release pressure from instrument with a single hand of the user.

* * * * *